(12) United States Patent
Kwak et al.

(10) Patent No.: US 8,598,347 B2
(45) Date of Patent: Dec. 3, 2013

(54) METHOD FOR MANUFACTURING DIPEPTIDYL PEPTIDASE-IV INHIBITOR AND INTERMEDIATE

(75) Inventors: Woo Young Kwak, Yongin-si (KR); Heung Jae Kim, Seongnam-si (KR); Jong Pil Min, Yongin-si (KR); Tae Hyun Yoon, Yongin-si (KR); Hyun Joo Shim, Yongin-si (KR); Moohi Yoo, Seoul (KR)

(73) Assignee: Dong-A Pharmaceutical. Co., Ltd, Seoul (KR)

( * ) Notice: Subject to any disclaimer, the term of this patent is extended or adjusted under 35 U.S.C. 154(b) by 0 days.

(21) Appl. No.: 13/260,179

(22) PCT Filed: Mar. 30, 2010

(86) PCT No.: PCT/KR2010/001948
§ 371 (c)(1),
(2), (4) Date: Sep. 23, 2011

(87) PCT Pub. No.: WO2010/114292
PCT Pub. Date: Oct. 7, 2010

(65) Prior Publication Data
US 2012/0016126 A1    Jan. 19, 2012

(30) Foreign Application Priority Data
Mar. 30, 2009 (KR) .................. 10-2009-0027106

(51) Int. Cl.
*C07D 241/08* (2006.01)
*C07C 323/58* (2006.01)
*C07C 227/10* (2006.01)

(52) U.S. Cl.
USPC ................ 544/384; 560/38; 560/30; 560/31; 560/16

(58) Field of Classification Search
USPC ............................ 544/384; 560/38, 30, 31, 16
See application file for complete search history.

(56) References Cited

FOREIGN PATENT DOCUMENTS

| WO | WO2004-083173 A2 | 9/2004 |
| WO | WO2006-098342 A1 | 9/2006 |

OTHER PUBLICATIONS

Biftu et al., (3R)-4-[(3R)-3-Amino-4-(2,4,5-trifluorophenyl)butanoyl]-3-(2,2,2-trifluoroethyl)-1,4-diazepan-2-one, a selective dipeptidyl peptidase IV inhibitor for the treatment of type 2 diabetes, Bioorganic & Medicinal Chemistry Letters, (2007), 17(1), pp. 49-52, ISSN: 0960-894X.
Jun et al., SAR Study of Beta-Aminoacyl-Containing Cyclic Hydrazide Derivatives as DPP-IV Inhibitors, Bulletin of Korean Chemical Society (2008), 29(11), pp. 2129-2134, ISSN: 0253-2964.

*Primary Examiner* — Kristin Vajda
(74) *Attorney, Agent, or Firm* — Lucas & Mercanti, LLP

(57) ABSTRACT

The present invention relates to an improved method for manufacturing dipeptidyl peptidase-IV inhibitor and intermediate. The present invention allows reduction of production costs by reacting low cost reagents, improves yield and is adaptable for mass production.

12 Claims, No Drawings

METHOD FOR MANUFACTURING DIPEPTIDYL PEPTIDASE-IV INHIBITOR AND INTERMEDIATE

CROSS-REFERENCE TO RELATED APPLICATIONS

This application is a 371 of PCT/KR2010/001948, filed on Mar. 30, 2010, which claims benefit of Korean Patent Application No. 10-2009-0027106, filed on Mar. 30, 2009, the contents of each of which are incorporated herein by reference.

BACKGROUND OF THE INVENTION

1. Field of the Invention

The present invention relates to an improved method for manufacturing dipeptidyl peptidase-IV inhibitor and an intermediate.

2. Description of the Related Art

DPP-IV is an enzyme functioned as a cleavage of N-terminal dipeptide of peptide having a terminal sequence of H-Xaa-Pro-Y (or H-Xaa-Ala-Y, where Xaa is any lipophilic amino acid, Pro is proline, and Ala is alanine) (Heins J et al. *Biophys Acta* 1988; 161), and also called DP-IV, DP-4, or DAP-IV. After finding out that DPP-IV degrades glucagon-like protein-1 (hereinafter, called as to GLP-1) that is known to have a powerful effect on a control function of insulin to blood glucose contents after dinner (Mentlein R et al. *Eur J Biochem* 1993:829-35), a possibility as very powerful therapeutic agent for Type II diabetes is presented, and then a study for developing DPP-IV inhibitor has become faster.

Merck Company developed triazolo piperazine compound with beta-amino acid structure, sitagliptin, during an investigation about DPP-IV inhibitor. The compound is the first DPP-IV inhibitor for treating Type II diabetes and has now become commercially available under a trademark, Januvia™, around the world after obtaining the new medicine approval from U.S. FDA in 2006. On this matter, Korean Patent Publication No. 2008-0094604 discloses that when triazolo piperazine part of sitagliptin is substituted with piperazinone containing hetero atom, it has an excellent DPP-IV inhibition activity, and also a significantly improved bioavailability as compared to that of the conventional DPP-IV inhibitor; and provides a heterocyclic compound containing new beta-amino group represented by the following Chemical Formula 1, or pharmaceutically acceptable salt thereof, a method for manufacturing the same, and a pharmaceutical composition, which contains the same as an effective component, for preventing and treating diabetes or obesity.

[Chemical Formula 1]

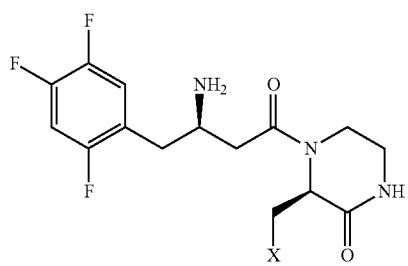

(In the above Chemical Formula 1, X is $OR^1$, $SR^1$ or $NR^1R^2$, where $R^1$ and $R^2$ are a lower alkyl of $C_1$-$C_5$, respectively; and in $NR^1R^2$, $R^1$ and $R^2$ may be 5-membered ring to 7-membered ring containing hetero atom, O.)

As shown in the following Reaction Formula A, Korean Patent Publication No. 2008-0094604 discloses a method for manufacturing heterocyclic compound represented by Chemical Formula 1 with beta-amino group, the method comprising I) preparing a compound represented by Chemical Formula 4 bonded with peptide bond by reacting a compound with beta-amino group represented by Chemical Formula 2 and a substituted heterocyclic compound represented by Chemical Formula 3 using 1-hydroxybenzotriazol (HOBT), 1-ethyl-3-(3-dimethylaminopropyl)carbodiimide (EDC), and tertiary amine; and II) reacting the compound represented by Chemical Formula 4 under an acid condition:

[Reaction Formula A]

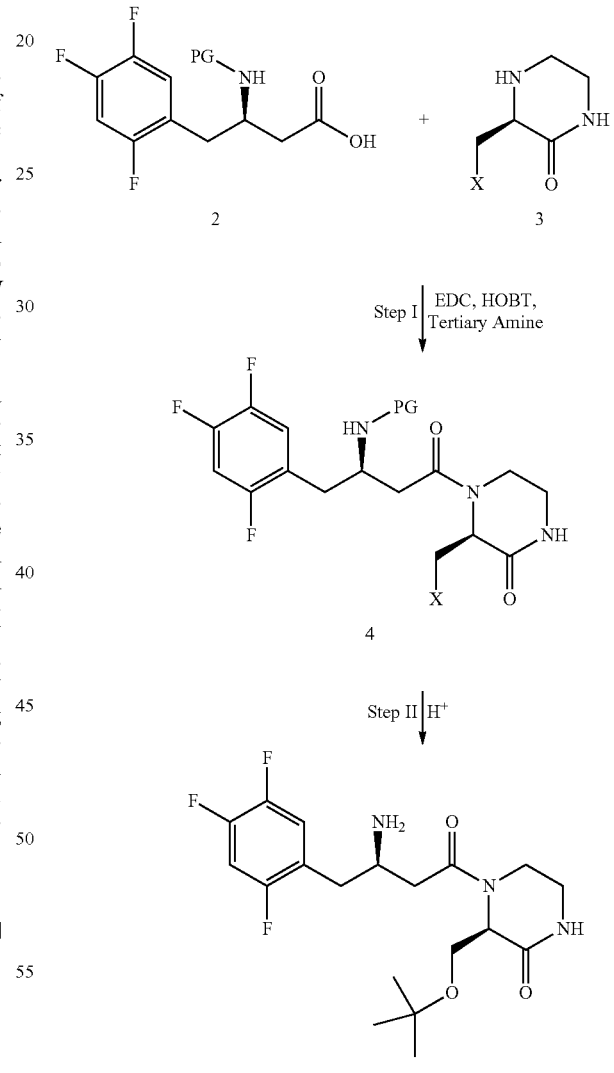

(In the above Reaction Formula A, X is the same as defined in the above Chemical Formula 1.)

At this time, the compound with beta-amino group represented by Chemical Formula 2 in the above Reaction Formula A may be used for manufacturing various DPP-IV inhibitors as disclosed in International Laying-Open Gazettes WO03/

000181, WO03/004498, WO03/082817, WO04/007468, WO04/032836, WO05/011581, WO06/097175, WO07/077, 508, WO07/063,928, WO08/028,662, WO08/087,560, and the like, besides the production of DPP-IV inhibitor represented by the above Chemical Formula 1, and may be produced through various methods.

For example, the compound represented by the above Chemical Formula 2 may be produced by using the method as disclosed in *J. Med. Chem.* 2005; 141 and Synthesis 1997; 873 as shown in the following Reaction Formula:

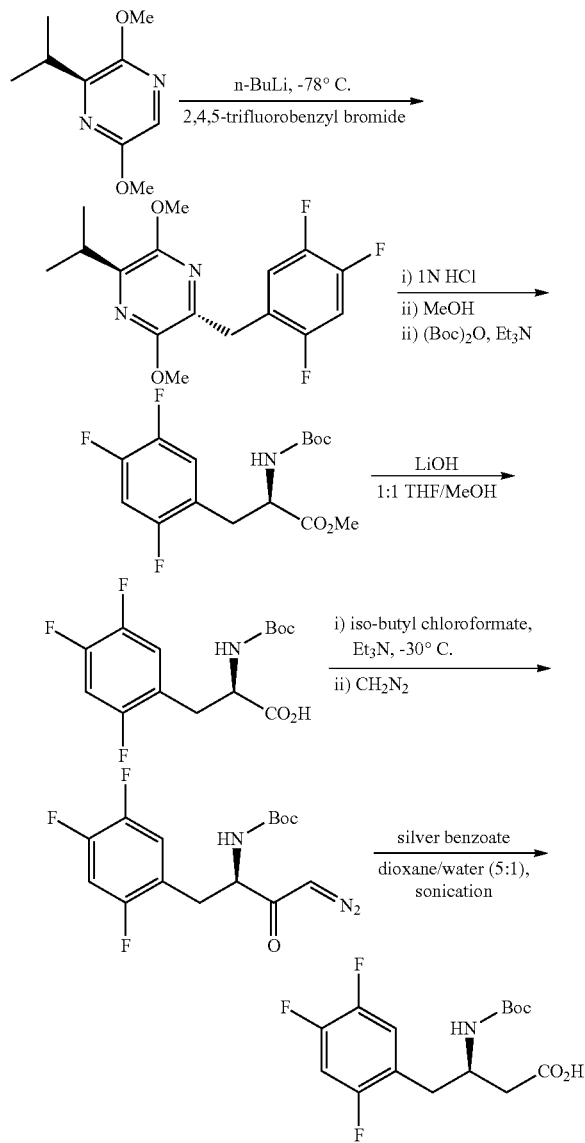

Specifically, ester compound is obtained through an amine-protecting reaction after reacting (2S)-(+)-2,5-dihydro-3,6-dimethoxy-2-isopropylpirazine with 2,4,5-trifluorobenzyl bromide and acid-treating. The ester compound may be again hydrolyzed to obtain 3-(2,4,5-trifluorophenyl)-2-aminopropionic acid; then diazoketone may be formed by using isobutyl chloroformate, tertiary amine such as triethyl amine or diisopropylethyl amine, and diazomethane; and the compound represented by Chemical Formula 2 may be produced by reacting the diazoketone with silver benzoate. However, the reaction as mentioned above has problems that it should be performed at low temperature (−78° C.), or should use an expensive alpha-amino acid and highly risky diazomethane.

Other method for manufacturing the compound represented by the above Chemical Formula 2 is also known in *Tetrahedron: Asymmetry* 2006; 205 or similarly *Bioorganic & Medicinal Chemistry Letters* 2007; 2622, as shown in the following Reaction Formula:

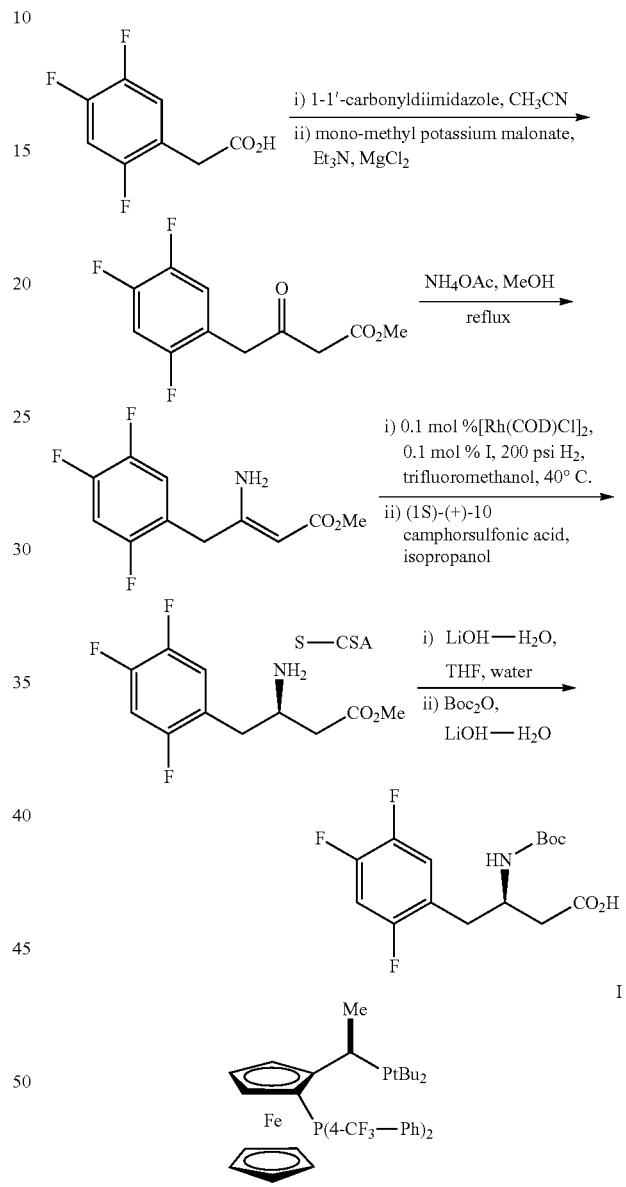

That is, 2,4,5-trifluorophenyl acetic acid is activated using 1,1'-carbonyldiimidazole, and then reacted with mono-methyl potassium malonate to produce beta-keto ester compound. The beta-keto ester compound is reacted with ammonium acetate and ammonium aqueous solution to produce enamine ester, and the ester compound is then reacted with chloro(1,5-cyclooctadiene)rhodium (I) dimer and chiral ferroceny ligand I through a high-pressure hydrogen reaction to produce the compound that is a beta-amino ester having chiral primary amine only. And then, the compound may be hydrolyzed to produce the compound represented by Chemical Formula 2. However, the above-described method has problem that the high-pressure hydrogen reaction should be performed by using an expensive metal catalyst.

In addition, the method for manufacturing the compound represented by Chemical Formula 2 is also disclosed in International Patent Publication No. WO 04/87650.

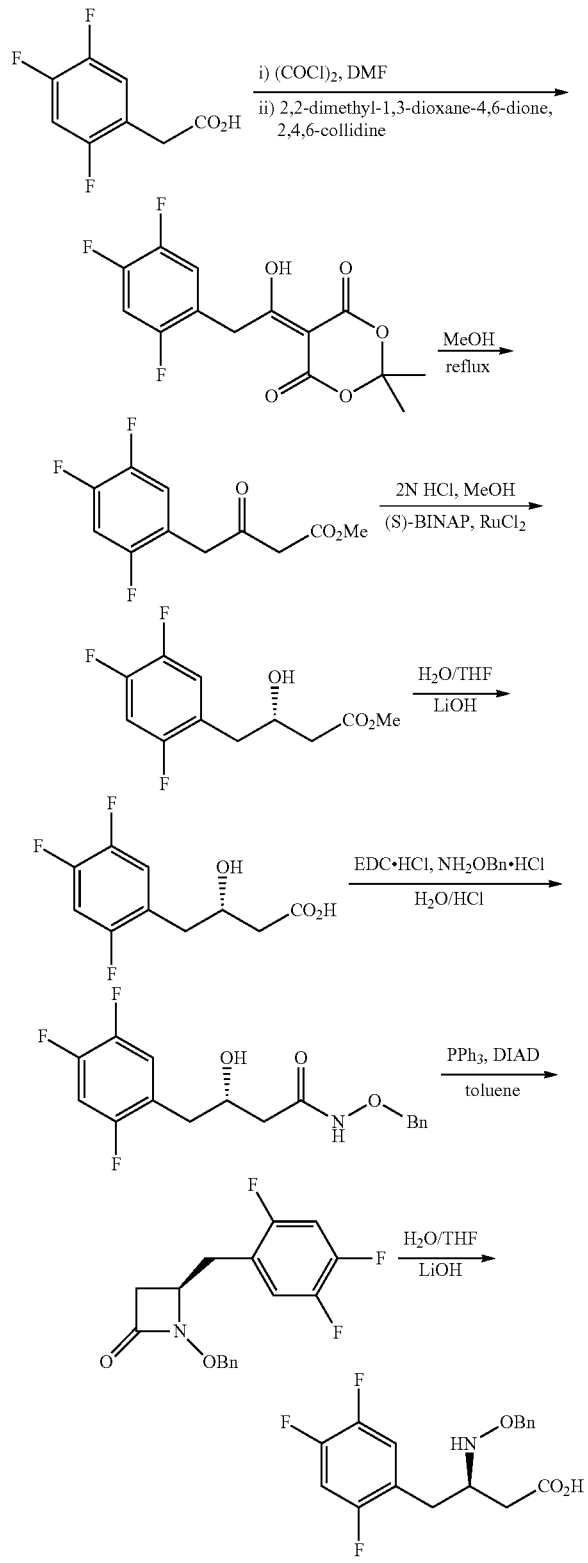

Specifically, 2,4,5-trifluorophenyl acetic acid is reacted with 2,2-dimethyl-1,3-dioxane-4,6-dione and oxalyl chloride that are an acid activation reagent and then the resulting product is refluxed in methanol to produce a compound corresponding thereto. The corresponding compound is reacted with (s)-BINAP-RuCl$_2$ that is a reduction reagent with enantioselectivity through a hydrogen reaction to produce a compound with (S)-coordination, and then the resulting compound is again hydrolyzed and then is coupling-reacted with O-benzylhydroxyamine to produce an intermediate. The intermediate produced as mentioned above may be subjected to a ring condensation reaction in the presence of triphenylphosphine and diisopropylazodicarboxylate and treated with lithium hydroxide aqueous solution to produce the compound represented by Chemical Formula 2 with (R)-coordination also in which an amine group is protected with O-benzyl. However, the above method has a problem that an overall process is long and tedious so that the yield of reaction is low and the reaction should be performed for a long period.

As mentioned above, the conventionally known method for manufacturing the compound represented by Chemical Formula 2 has several problems such as use of an expensive reagent, long synthesizing time, and low yield, and thus it is not sufficient for a commercial mass-production.

Furthermore, the compound represented by Chemical Formula 3 may be produced by using the following Reaction Formula as disclosed in Korean Patent Publication No. 2008-0094604:

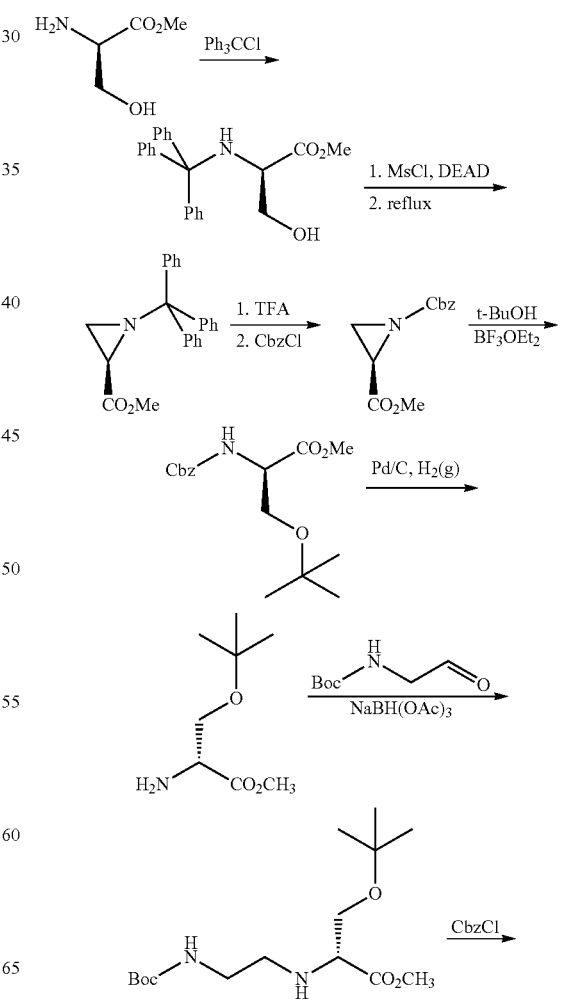

-continued

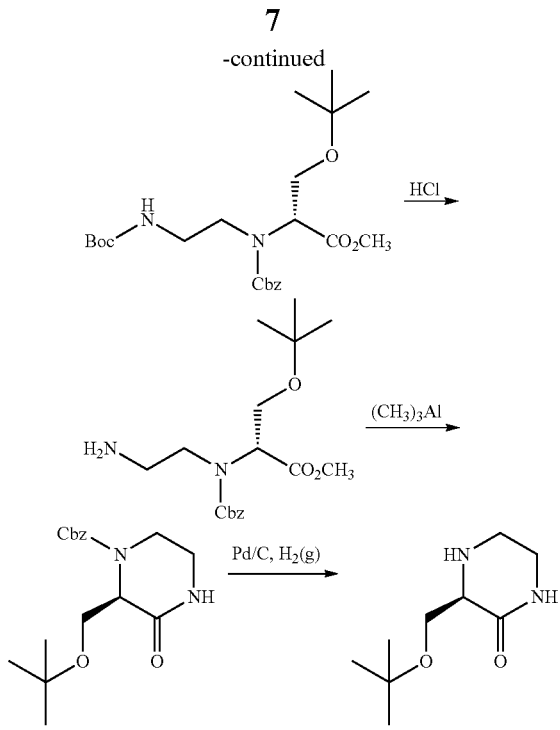

(In the above Reaction Formula, X is the same as defined in the Chemical Formula 1.)

Specifically, D-serine methyl ester compound, which is a starting material, is substituted with trityl chloride; then hydroxyl group is again substituted with mesyl group, and then refluxed to convert to aziridine compound.

The trityl group is removed from the aziridine compound by using trifluoroacetic acid; then the aziridine compound is protected with benzyloxycarbonyl (Cbz), and then is reacted with HX; and Cbz is de-protected to obtain methyl 2-amino-3-substituted carbonate. The intermediate may be produced by using the compound produced by protecting the secondary amine of the compound produced through reacting N-butyloxycarbonyl-2-amino acetaldehyde with a reduction reagent (sodiumcyanoborohydride, sodiumtriacetoxyborohydride, sodiumborohydride, and the like) and the compound, of which secondary amine is protected with benzyloxycarbonyl (Cbz), and the compound of which butyloxycarbonyl (Boc) is de-protected. The compound produced as mentioned above is subjected to a cyclization with trimethyl aluminum (or diisopropylethylamine/ethanol, sodium hydrogen carbonate/methanol, and the like) to de-protect Cbz so that the compound represented by Chemical Formula 3 may be obtained.

However, the above method has a problem that it also uses an expensive reagent, the time for synthesizing is long, and the yield is low so that it is not suitable for a commercial mass-production.

Furthermore, since 1-hydroxybenzotriazol (HOBT) and 1-ethyl-3-(3-dimethylaminopropyl) carbodiimide (EDC) used for producing the conventional compound represented by Chemical Formula 1 are an expensive reagent, the cost for reaction is high so that it is not suitable for a commercial mass-production.

For this reason, the present inventors completed the present invention by confirming that the compound represented by Chemical Formula 1 can be economically produced with high yield by using the new method for manufacturing the compounds represented by Chemical Formula 2 and Chemical Formula 3 used with cheaper reagents during the study for a manufacturing method suitable for a commercial mass-production, in which the method uses cheaper reagents; is an economical method; and improves a yield.

SUMMARY OF THE INVENTION

One object of the present invention is to provide a method for manufacturing a useful compound as an intermediate for manufacturing dipeptidyl peptidase-IV inhibitor.

Another object of the present invention is to provide an improved method for manufacturing dipeptidyl peptidase-IV inhibitor.

In order to achieve the objects, the present invention provides a new method for manufacturing an intermediate of dipeptidyl peptidase-IV inhibitor.

The present invention also provides an improved method for manufacturing dipeptidyl peptidase-IV inhibitor.

The present invention can be useful for mass-production through reducing the production cost by using cheaper reagents on the reaction and improving the yield.

DESCRIPTION OF THE PREFERRED EMBODIMENTS

Hereinafter, the present invention will be described in detail.

The present invention provides a new method for manufacturing an intermediate of depeptidyl peptidase-IV inhibitor represented by Chemical Formula 2, as shown in the following Reaction Formula 1, the method comprising: (Step a) preparing a compound represented by Chemical Formula 6 by ring-opening of aziridine ring using Grignard reagent in a compound represented by Chemical Formula 5; and (Step b) preparing a compound represented by Chemical Formula 2 by introducing an amine-protecting group after hydrolyzing a compound represented by Chemical Formula 6,

[Reaction Formula 1]

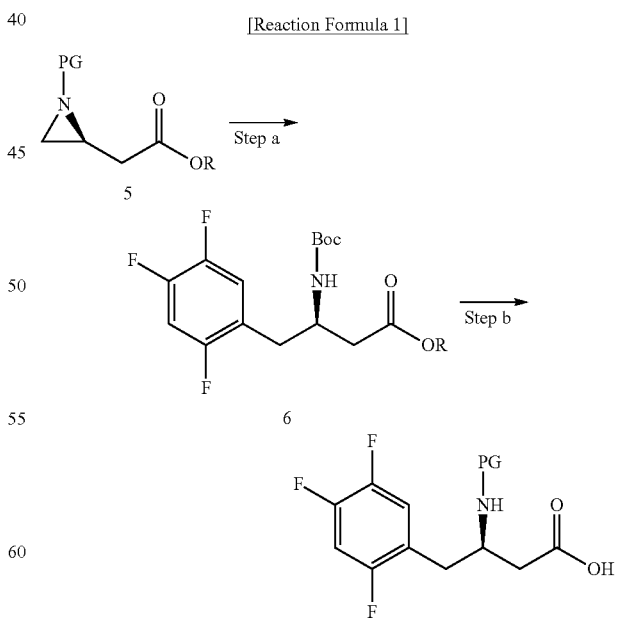

(In the above Reaction Formula 1, PG is a protecting group, and R is a lower alkyl of $C_1$-$C_5$.)

Specifically, in the above Step a, the aziridine compound represented by Chemical Formula 5 is reacted with 2,4,5-trifluorophenyl magnesium bromide reagent in the presence of copper bromide (I) dimethyl sulfide complex to produce a ester compound represented by Chemical Formula 6. At this time, the compound represented by Chemical Formula 5 can be commercially purchased or produced by using the known method in the art in which the present invention belongs to. For example, by using methods disclosed in Tetrahedron Letter 1991; 923, Tetrahedron Letter 1993; 6513, Tetrahedron Letter 1992; 6389, Tetrahedron Letter 2004; 821, Tetrahedron Letter 2006; 3509, and the like, acid functional group of N-Boc L-aspartic acid t-butyl ester is activated with isobutylchloroformate at −40° C. to room temperature, and then reacted with sodiumborohydride, i.e., a reduction reagent, to thereby produce a compound of which acid functional group is substituted by alcohol group. And then, the produced compound may be reacted with triphenyl phosphine and diisopropylazodicarboxylate (DIAD) to obtain the compound represented by Chemical Formula 5.

Next, in Step b, the compound represented by Chemical Formula 6 is hydrolyzed under the condition of acid such as trifluoroacetic acid, hydrochloric acid, sulfuric acid, and the like, and then an amine-protecting group may be introduced to produce the compound represented by Chemical Formula 2. At this time, butoxycarbonyl (Boc) or benzyloxycarbonyl (Cbz) may be used as the amine-protecting group.

In addition, the present invention provides a new method for manufacturing an intermediate of dipeptidyl peptidase-IV inhibitor represented by Chemical Formula 3, as shown in the following Reaction Formula 2, the method comprising: (Step a') preparing a compound represented by Chemical Formula 8 by reacting a compound represented by Chemical Formula 7 with an amine group-protected aminoaldehyde compound and a reduction reagent; and (Step b') preparing a compound represented by Chemical Formula 3 or salt thereof by removing the amine-protecting group by triggering a hydrogen reaction in a compound represented by Chemical Formula 8 and inducing a cyclization,

[Reaction Formula 2]

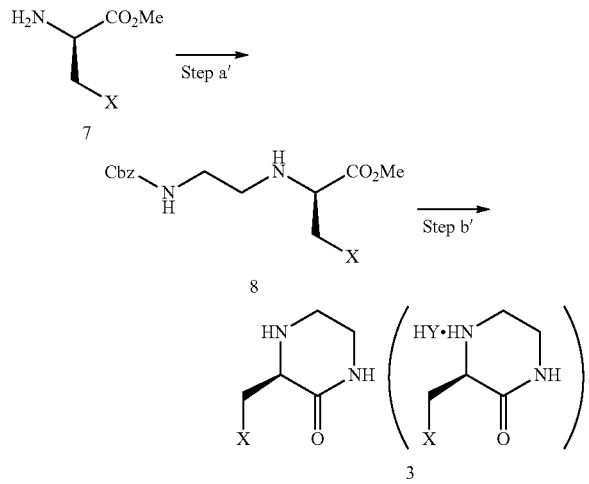

(In the above Reaction Formula 2, X is the same as defined in the above Chemical Formula 1, and HY is a free acid.)

Specifically, in the above Step a', the compound represented by Chemical Formula 7 is reacted with the amine group-protected aminoaldehyde compound and a reduction reagent to produce the compound represented by Chemical Formula 8. At this time, the compound represented by Chemical Formula 7 may be commercially purchased or produced by using the known method in the art in which the present invention belongs to. For example, when X is t-butoxy, D-serine methyl ester hydrochloride is reacted with sodium hydrogen carbonate and benzyloxychloroformate in the presence of tetrahydrofuran at 0° C. to room temperature to protect an amine group, then reacted with isobutyrene gas in the presence of sulfuric acid catalyst at 0° C. to room temperature to produce an intermediate, and then is subjected to hydrogenation in the presence of palladium/carbon catalyst to produce the compound represented by Chemical Formula 7. At this time, the amine group-protected amionaldehyde compound may be aminoaldehyde compound, which can be commercially purchased, of which the amine group is protected with Cbz, and is reacted with the compound represented by Chemical Formula 7 in the presence of sodiumcyanoborohydride and zinc chloride that are the reduction reagent to obtain the compound represented by Chemical Formula 8.

Next, in the above Step b', the amine-protecting group is removed from the compound represented by Chemical Formula 8 by causing hydrogenation, and simultaneously the cyclization is induced to produce the compound represented by Chemical Formula 3. At this time, the hydrogenation is preferably performed in the presence of palladium/carbon. In addition, the compound represented by Chemical Formula 3 may be used in the form of acceptable salt, and an acid addition salt that is produced by a free acid is useful as a salt. Organic acid or inorganic acid may be used as the free acid. At this time, the inorganic acid may include hydrochloric acid, bromic acid, sulfuric acid, phosphoric acid, and the like, and the organic acid may include di-p-toluoyl-L-tartrate, citric acid, acetic acid, lactic acid, maleic acid, fumaric acid, gluconate, methanesulfonic acid, acetic acid, glycolic acid, succinic acid, tartaric acid, 4-toluene sulfonic acid, glacturonic acid, embonic acid, glutamic acid, aspartic acid, and the like.

In addition, the present invention provides a compound represented by the following Chemical Formula 8 that is produced as an intermediate when producing the compound represented by Chemical Formula 2.

[Chemical Formula 8]

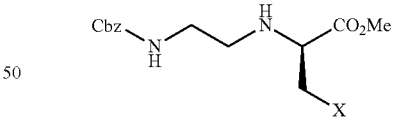

(In the above Chemical Formula 8, X is the same as defined in the above Chemical Formula 1.)

Furthermore, the present invention provides an improved method for manufacturing dipeptidyl peptidase-IV inhibitor represented by Chemical Formula 1, as shown in the following Reaction Formula 3, the method comprising: (Step 1) preparing the compound represented by Chemical Formula 4 by bonding the compound represented by Chemical Formula 2 and the compound represented by Chemical Formula 3 with peptide bond by reacting them with isochloroformate and a base in the presence of a reaction solvent; and (Step 2) preparing the compound represented by Chemical Formula 1 by removing an amine-protecting group of the compound represented by Chemical Formula 4 produced in the above Step 1,

[Reaction Formula 3]

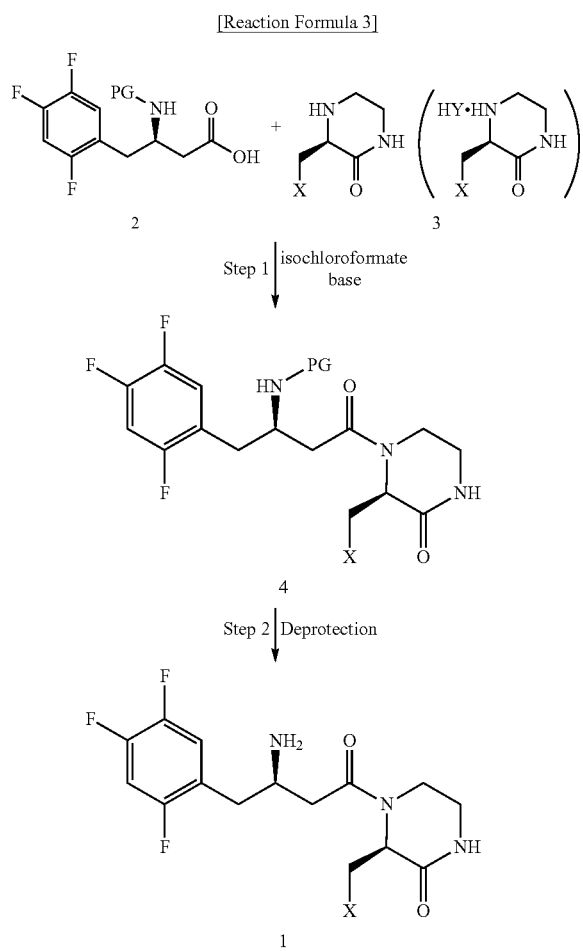

(In the above Reaction Formula 3, PG is a protecting group, X is the same as defined in the above Chemical Formula 1, and HY is the same as defined in the above Reaction Formula 2.)

Firstly, Step 1 is to produce the compound represented by Chemical Formula 4 by bonding the compound represented by Chemical Formula 2 and the compound represented by Chemical Formula 3 with peptide bond through the reaction of them using isochloroformate and a base.

For the present invention, the reaction solvent may include toluene, tetrahydrofuran, methylene chloride, acetonitrile, N,N-dimethylformamide, and the like.

For the present invention, the base may include more than one selected from the group consisting of tertiary amines, such as N-methyl morpholine, isopropylethylamine, triethylamine, pyridine, and the like.

For the present invention, the compound represented by Chemical Formula 2 or 3 may be commercially purchased or produced by using the known method, or the method as disclosed in the above Reaction Formula 1 or Reaction Formula 2.

For the present invention, the reaction of the above Step 1 is preferably performed at −20° C. to room temperature, and in the case of get out of the above range, there is a problem that the reaction is difficultly processed so that the yield is reduced.

Next, Step 2 is to provide the compound represented by Chemical Formula 1 by removing the amine-protecting group from the compound represented by Chemical Formula 4 produced in the above Step 1.

The removal of protecting group in the above Step 2 may be performed under an acid condition or through hydrogenation. Specifically, when the amine-protecting group is butoxycarbonyl (Boc), it may be removed by reacting under the condition of acid, such as trifluoroacetic acid/dichloromethane, ethyl acetate/hydrogen chloride, diethylether/hydrogen chloride, hydrogen chloride/dichloromethane, methanol/hydrogen chloride, and the like; and when the amine-protecting group is benzyloxycarbonyl (Cbz), the protecting group may be removed through a hydrogenation in the presence of palladium/carbon.

Dipeptidyl peptidase-IV inhibitor of the present invention represented by Chemical Formula 1 may be used in the form of pharmaceutically acceptable salt, and an acid addition salt produced by pharmaceutically acceptable free acid is useful as a salt. Inorganic acid and organic acid may be used as a free acid. Inorganic acid may include hydrochloric acid, bromic acid, sulfuric acid, phosphoric acid, and the like, and organic acid may include citric acid, acetic acid, lactic acid, maleic acid, fumaric acid, gluconate, methanesulfonic acid, acetic acid, glycolic acid, succinic acid, tartaric acid, 4-toluene sulfonic acid, glacturonic acid, embonic acid, glutamic acid, aspartic acid, and the like. Preferably, hydrochloric acid may be used as inorganic acid and tartaric acid may be used as organic acid.

The addition salt according to the present invention may be produced by using a general method. For example, the compound represented by Chemical Formula 1 is dissolved in water-miscible organic solvent, such as acetone, methanol, ethanol, acetonitrile, and the like; excess organic acid, or acid solution of inorganic acid is added thereto; and then precipitated or crystallized to produce the addition salt. Subsequently, solvent or excess acid is evaporated from the above mixture and then the mixture may be dried or the precipitated salt may be suction-filtered to obtain the addition salt.

After producing the intermediates or the compounds represented by Chemical Formulas 1-3 according to the present invention, their molecular structures may be determined by using Infrared Spectroscopy, Proton Nuclear Magnetic Resonance Spectrum, Mass Spectrometry, Liquid Chromatography, X-Ray Structure Determination Method, Polarimeter, and Comparison between the calculated value and actual value of elemental analysis of represented compounds.

As mentioned above, the manufacturing method according to the present invention can reduce the cost for manufacturing the compound represented by Chemical Formula 1 due to the use of cheaper reagents, and also improve the yield so that it can be used in useful to mass-production.

Hereinafter, the present invention will be described in more detail with reference to Examples. However, the following Examples are only for illustrating, but the present invention is not limited thereto.

Example 1

Preparation of (R)-3-(t-butoxycarbonylamino)-4-(2,4,5-trifluorophenyl)butanoic acid (Chemical Formula 2) from (S)-4-t-butoxy-2-(t-butoxycarbonylamino)-4-oxobutanoic acid Step 1: Preparation of (S)-t-butyl 3-(t-butoxycarbonylamino)-4-hydroxybutanoate 2.0 g of (S)-4-t-butoxy-2-(t-butoxycarbonylamino)-4-oxobutanoic acid and 14 mL of tetrahydrofuran were added to 50 mL flask and then the resulting reaction solution was cooled to 0° C. While the reaction solution was stirred, 1.0 mL of 4-methylmorpholine was dropped, and after 10 minutes, 1.2 mL of isobutylchloroformate was dropped, and then stirred for 1 hour. The produced solid was filtered with diatomite, was washed with 14 mL of tetrahydrofuran, and then the filtrate was cooled to 0° C. 523 mg of sodium borohydride was added to the cooled filtrate, and stirred for 4 hours while the reaction temperature was naturally increased to room temperature. After completing the reaction, the reaction solution was cooled to 0° C. and then 10 mL of ammonium chloride aqueous solution was dropped. 20 mL of ethyl acetate and 10 mL of water were added and then stirred for 10 minutes. An organic layer was isolated, dehydrated with magnesium sulfate and then concentrated under reduced pressure. A concentrated residue was isolated with column chromatography (n-hexane:ethyl acetate=2:1) and then concentrated under reduced pressure to obtain 1.86 g of a title compound.

$^1$H NMR (CDCl$_3$, 400 MHz) δ 5.19 (s, 1H), 3.94 (br, 1H), 3.67 (s, 2H), 2.46 (m, 3H), 1.43 (s, 9H), 1.42 (s, 9H)

Step 2: Preparation of (S)-t-butyl 2-(2-t-butoxy-2-oxoethyl)aziridine-1-carboxylate (Chemical Formula 5)

2.90 g of triphenylphosphine and 15 mL of tetrahydrofuran were added to 100 mL flask and the resulting reaction solution was cooled to 0° C. 2.17 mL of diisopropylazodicarboxylate was dropped while the reaction solution was stirred. After 30 minutes, 10 mL of tetrahydrofuran solution with 1.52 g of (S)-t-butyl 3-(t-butoxycarbonylamino)-4-hydroxybutanoate was dropped and stirred for 16 hours while the reaction temperature was naturally increased to room temperature. After completing the reaction, 40 mL of ethyl acetate and 40 mL of water were added to the reaction solution and then stirred for 10 minutes. An organic layer was isolated, dehydrated with magnesium sulfate, and then concentrated under reduced pressure. A concentrated residue was isolated with column chromatography (n-hexane:ethyl acetate=15:1) and then concentrated under reduced pressure to obtain 1.04 g of a title compound.

$^1$H NMR (CDCl$_3$, 400 MHz) δ 2.69 (m, 1H), 2.61 (dd, 1H), 2.31 (d, 1H), 2.16 (dd, 1H), 1.97 (d, 1H), 1.44 (d, 18H)

Step 3: Preparation of (R)-t-butyl 3-(t-butoxycarbonylamino)-4-(2,4,5-trifluorophenyl)butanoate (Chemical Formula 6)

4.2 mL of 1-bromo-2,4,5-trifluorobenzene and 10.8 mL of tetrahydrofuran were added to 50 mL flask and the resulting reaction solution was cooled to 0° C. 15 mL of isopropylmagnesium chloride [2.0 M tetrahydrofuran solution] was dropped to the reaction solution under nitrogen atmosphere and stirred for 30 minutes to produce Grignard reagent. 1.95 g of (S)-t-butyl 2-(2-t-butoxy-2-oxoethyl)aziridine-1-carboxylate and 50 mL of tetrahydrofuran were added to another 250 mL flask and the resulting reaction solution was cooled to 0° C. And then, 778 mg of copper (I) bromide dimethylsulfide complex was added. 22.7 mL of the Grignard reagent produced under nitrogen atmosphere was dropped, and stirred for 6 hours while the reaction temperature was maintained at 0° C. After completing the reaction, 50 mL of ammonium chloride aqueous solution was dropped to the reaction solution; 100 mL of ethyl acetate and 50 mL of water were added and then stirred for 10 minutes. An organic layer was isolated, dehydrated with magnesium sulfate, and then concentrated under reduced pressure. A concentrated residue was isolated with column chromatography (n-hexane:ethyl acetate=20:1) and then concentrated under reduced pressure to obtain 2.62 g of a title compound.

$^1$H NMR (CDCl$_3$, 400 MHz) δ 7.02 (m, 1H), 6.87 (m, 1H), 5.11 (br, 1H), 4.07 (br, 1H), 2.82 (dd, 1H), 2.77 (dd, 1H), 2.45 (dd, 1H), 2.35 (dd, 1H), 1.44 (s, 9H), 1.35 (s, 9H)

Step 4: Preparation of (R)-3-(t-butoxycarbonylamino)-4-(2,4,5-trifluorophenyl)butanoic acid (Chemical Formula 2)

1.31 g of (R)-t-butyl 3-(t-butoxycarbonylamino)-4-(2,4,5-trifluorophenyl)butanoate, 16 mL of methylene chloride, and 16 mL of trifluoroacetic acid were added to 100 mL flask and the resulting reaction solution was stirred for 6 hours. After completing the reaction, the reaction solution was concentrated under reduced pressure and 16 mL of methanol was added to the concentrated residue. The reaction solution was cooled to 0° C., 2.82 g of sodium hydrogen carbonate and 0.77 mL of di-t-butyl dicarbonate were added, and then stirred for 6 hours while the reaction temperature was naturally increased to room temperature. After completing the reaction, the reaction solution was concentrated under reduced pressure; then 30 mL of ethyl acetate and 30 mL of water were added; and then stirred for 10 minutes. An aqueous layer was isolated, cooled to 0° C., and then 2 N hydrochloric acid aqueous solution was dropped to adjust to pH 3-4. The aqueous layer was extracted with methylene chloride:methanol=10:1 solvent, dehydrated with magnesium sulfate, and then concentrated under reduced pressure to obtain 828 mg of a title compound.

$^1$H NMR (CDCl$_3$, 400 MHz) δ 7.04 (m, 1H), 6.89 (m, 1H), 6.08 (br, 1H), 5.04 (br, 1H), 4.13 (br, 1H), 2.88 (br, 2H), 2.62 (m, 2H), 1.36 (s, 18H)

Mass (M+Na): 356

Example 2

Preparation of (R)-3-(benzyloxycarbonylamino)-4-(2,4,5-trifluorophenyl)butanoic acid (Chemical Formula 2) from (S)-4-t-butoxy-2-(t-butoxycarbonyl)-4-oxobutanoic acid 64 mg of 3-(t-butoxycarbonylamino)-4-(2,4,5-trifluorophenyl)butanoate was produced by using the same method with that of Steps 1 to 3 of Example 1. For Step 4 of Example 1, tetrahydrofuran/water and N-(benzyloxycarbonyloxy)succinimide were used instead of methanol and di-t-butyl dicarbonate, respectively, to obtain 40 mg of a title compound.

$^1$H NMR (CDCl$_3$, 400 MHz) δ 7.45-7.18 (m, 5H), 7.05 (m, 1H), 6.83 (m, 1H), 5.37 (d, 1H), 5.10 (s, 2H), 4.52-4.16 (m, 1H), 3.01-2.85 (m, 2H), 2.78-2.42 (m, 2H)

Mass (M+1): 368

Example 3

Preparation of (R)-3-(t-butoxycarbonylamino)-4-(2,4,5-trifluorophenyl)butanoic acid (Chemical Formula 2) from (S)-4-benzyloxy-2-(t-butoxycarbonylamion)-4-oxobutanoic acid Step 1: Preparation of (S)-benzyl 3-(t-butoxycarbonylamino)-4-hydroxybutanoate 402 mg of a title compound was obtained by using the same method with that of Step 1 of Example 1, except that (S)-4-(benzyloxy)-2-(t-butoxycarbonylamino)-4-oxobutanoic acid (500 mg) was used instead of (S)-4-t-butoxy-2-(t-butoxycarbonylamino)-4-oxobutanoic acid in Step 1 of Example 1.

$^1$H NMR (CDCl$_3$, 400 MHz) δ 7.27 (m, 5H), 5.16 (m, 3H), 4.00 (m, 1H), 3.68 (m, 2H) 2.66 (m, 2H), 2.40 (s, 1H), 1.41 (s, 9H)

Step 2: Preparation of (S)-t-butyl 2-(2-benzyloxy-2-oxoethyl)aziridine-1-carboxylate (Chemical Formula 5)

239 mg of a title compound was obtained by using the same method with that of Step 2 of Example 1, except that (S)-benzyl 3-(t-butoxycarbonylamion)-4-hydroxybutanoate (402 mg) was used instead of (S)-t-butyl 3-(t-butoxycarbonylamino)-4-hydroxybutanoate in Step 2 of Example 1.

$^1$H NMR (CDCl$_3$, 400 MHz) δ 7.34 (m, 5H), 5.13 (m, 2H), 2.59 (m, 2H) 2.37 (m, 2H), 1.99 (d, 1H), 1.43 (s, 9H)

Step 3: Preparation of (R)-benzyl 3-(t-butoxycarbonylamino)-4-(2,4,5-trifluorophenyl)butanoate (Chemical Formula 6)

58 mg of a title compound was obtained by using the same method with that of Step 3 of Example 1, except that (S)-t-butyl 2-(2-benzyloxy-2-oxoethyl)aziridine-1-carboxylate (100 mg) was used instead of (S)-t-butyl 2-(2-t-butoxy-2-oxoethyl)aziridine-1-carboxylate in Step 3 of Example 1.

$^1$H NMR (CDCl$_3$, 400 MHz) δ 7.37 (m, 5H), 6.96 (m, 1H), 6.86 (m, 1H), 5.11 (m, 3H), 4.12 (m, 1H), 2.81 (m, 2H) 2.56 (m, 2H), 1.35 (s, 9H)

Step 4: Preparation of (R)-3-(t-butoxycarbonylamino)-4-(2,4,5-trifluorophenyl)butanoic acid (Chemical Formula 2)

58 mg of (R)-benzyl 3-(t-butoxycarbonylamino)-4-(2,4,5-trifluorophenyl)butanoate, 3 mL of methanol, and 20 mg of 10 wt % palladium/carbon were added to 25 mL flask and the resulting reaction solution was stirred. A hydrogen gas was bubbled for 2 hours at room temperature; the reaction solution was filtered by passing through celite, washed with 15 mL of ethyl acetate, and the filtrate was concentrated under reduced pressure to obtain 44 mg of a title compound.

$^1$H NMR (CDCl$_3$, 400 MHz) δ 7.04 (m, 1H), 6.89 (m, 1H), 6.08 (br, 1H), 5.04 (br, 1H), 4.13 (br, 1H), 2.88 (br, 2H), 2.62 (m, 2H), 1.36 (s, 18H)

Mass (M+Na): 356

Example 4

Preparation of (R)-3-(t-butoxycarbonylamino)-4-(2,4,5-trifluorophenyl)butanoic acid (Chemical Formula 2) from (S)-2-(t-butoxycarbonylamino)-4-methoxy-4-oxobutanoic acid

Step 1: Preparation of (S)-methyl 3-(t-butoxycarbonylamino)-4-hydroxybutanoate 1.23 g of a title compound was obtained by using the same method with that of Step 1 of Example 1, except that (S)-2-(t-butoxycarbonylamino)-4-methoxy-4-oxobutanoic acid (2.0 g) was used instead of (S)-4-t-butoxy-2-(t-butoxycarbonylamino)-4-oxobutanoic acid in Step 1 of Example 1.

$^1$H NMR (CDCl$_3$, 400 MHz) δ 5.19 (s, 1H), 3.97 (m, 1H), 3.68 (m, 5H), 2.62 (m, 2H), 2.45 (s, 1H), 1.42 (s, 9H)

Step 2: Preparation of (S)-t-butyl 2-(2-methoxy-2-oxoethyl)aziridine-1-carboxylate (Chemical Formula 5)

820 mg of a title compound was obtained by using the same method with that of Step 2 of Example 1, except that (S)-methyl 3-(t-butoxycarbonylamino)-4-hydroxybutanoate (1.23 g) was used instead of (S)-t-butyl 3-(t-butoxycarbonylamino)-4-hydroxybutanoate in Step 2 of Example 1.

$^1$H NMR (CDCl$_3$, 400 MHz) δ 3.68 (s, 3H), 2.72 (m, 1H), 2.65 (dd, 1H), 2.35 (m, 2H), 1.98 (d, 1H), 1.43 (s, 9H)

Step 3: Preparation of (R)-methyl 3-(t-butoxycarbonylamino)-4-(2,4,5-trifluorophenyl)butanoate (Chemical Formula 6)

53 mg of a title compound was obtained by using the same method with that of Step 3 of Example 1, except that (S)-t-butyl 2-(2-methoxy-2-oxoethyl)aziridine-1-carboxylate (70 mg) was used instead of (S)-t-butyl 2-(2-t-butoxy-2-oxoethyl)aziridine-1-carboxylate in Step 3 of Example 1.

$^1$H NMR (CDCl$_3$, 400 MHz) δ 6.96 (m, 1H), 6.87 (m, 1H), 5.09 (br, 1H), 4.10 (br, 1H), 3.69 (s, 3H), 2.83 (m, 2H), 2.56 (m, 2H), 1.36 (s, 9H)

Step 4: Preparation of (R)-3-(t-butoxycarbonylamino)-4-(2,4,5-trifluorophenyl)butanoic acid (Chemical Formula 2)

53 mg of (R)-methyl 3-(t-butoxycarbonylamino)-4-(2,4,5-trifluorophenyl)butanoate, 1.5 mL of tetrahydrofuran, and 0.5 mL of water were added to 25 mL flask and the resulting reaction solution was cooled to 0° C. 7.32 mg of lithium hydroxide was added to the reaction solution and stirred for 6 hours while the reaction temperature was naturally increased to room temperature. After completing the reaction, 5 mL of ethyl acetate and 5 mL of water were added to the reaction solution and stirred for 10 minutes. An aqueous layer was isolated, cooled at 0° C., and 2 N hydrochloric acid aqueous solution was dropped to adjust to pH 3-4. The aqueous layer was extracted with methylene chloride:methanol=10:1 solvent, dehydrated with magnesium sulfate, and then concentrated under reduced pressure to obtain 40.8 mg of a title compound.

$^1$H NMR (CDCl$_3$, 400 MHz) δ 7.04 (m, 1H), 6.89 (m, 1H), 6.08 (br, 1H), 5.04 (br, 1H), 4.13 (br, 1H), 2.88 (br, 2H), 2.62 (m, 2H), 1.36 (s, 18H)

Mass (M+Na): 356

Example 5

Preparation of (R)-3-(t-butoxymethyl)piperazine-2-one or Salt Thereof (Chemical Formula 3)

Step 1: Preparation of (R)-methyl 2-(benzyloxycarbonylamino)-3-t-butoxypropanoate 130 L of methylene chloride was added; 20.5 g of (R)-methyl 2-(benzyloxycarbonylamino)-3-hydroxypropanate to a reactor; then stirred for 30 minutes; and then 0.4 kg of sulfuric acid was added. Isobutylene gas was bubbled for 24 hours while its temperature was maintained at 20-25° C. After completing the reaction, 18 L of saturated sodium hydrogen carbonate aqueous solution was slowly added, stirred for 1 hour, and then an organic layer was isolated. 5 kg of sodium sulfate was added to the organic layer, stirred for 1 hour, filtered, washed, and then the filtrate was concentrated under reduced pressure to obtain 29.3 kg of a title compound.

$^1$H NMR (CDCl$_3$, 400 MHz) δ 7.36-7.30 (m, 5H), 5.59 (d, 1H), 5.10 (s, 2H), 4.44 (m, 1H), 3.80 (m, 1H), 3.73 (s, 3H), 3.56 (m, 1H), 1.10 (s, 9H)

Step 2: Preparation of (R)-methyl 2-amino-3-t-butoxypropanoate (Chemical Formula 7)

330.0 L of methanol was added and 66.0 kg of (R)-methyl 2-(benzyloxycarbonylamino)-3-t-butoxypropanoate was added to a hydrogen reactor; and then purged with nitrogen. 4.95 kg of palladium/carbon (10% water mixture) was added and hydrogen was filled to maintain at 5 bar of pressure. It was stirred for 60 minutes, filtered, washed, and then concentrated under reduced pressure. 132.0 L of ethyl acetate and 88 L of water were added to a concentrated residue; stirred for 10 minutes; an organic layer was isolated (in 6 times), dehydrated, and then concentrated under reduced pressure to obtain 27.5 kg of a title compound.

$^1$H NMR (CDCl$_3$, 400 MHz) δ 4.21 (m, 1H), 3.82 (s, 3H), 3.74-3.88 (m, 2H), 1.20 (s, 9H)

Step 3: Preparation of (R)-methyl 2-(2-(benzyloxycarbonylamino)ethylamino)-3-t-butoxypropanoate (Chemical Formula 8)

155 L (122.5 kg) of methanol and 5.04 kg of sodiumcyanoborohydride were added to a first reactor, cooled to less than 0° C., and then 5.47 kg of zinc chloride was added. 155 L of methanol and 31 kg of 2-oxoethylcarbamate were added to a second reactor, cooled to 0° C., and then 28.1 kg of (R)-methyl 2-amino-3-t-butoxypropanoate was added. The solution produced in the first reactor was immediately dropped to the second reactor; its temperature was increased to room temperature, and then stirred for 2 hours. After completing the reaction, the reaction solution was concentrated under reduced pressure; 93 L of ethyl acetate and 186 L of isopropylether were added; stirred for 5 minutes; the resulting solid was filtered with celite pad; and then washed with isopropylether:ethyl acetate=2:1 (93 L). The filtrate was washed with 310 L of saturated sodium hydrogen carbonate in 7 times and then washed with 310 L of brine. An organic layer was dehydrated with 50.0 kg of sodium sulfate, filtered, washed, and then concentrated under reduced pressure to obtain 35.5 kg of a title compound.

$^1$H NMR (CDCl$_3$, 400 MHz) δ 7.36-7.28 (m, 5H), 5.09 (s, 2H), 3.72 (s, 3H), 3.71-3.52 (m, 3H), 3.33 (m, 4H), 1.13 (s, 9H)

Step 4: Preparation of (R)-3-(t-butoxymethyl)piperazine-2-one (Chemical Formula 3)

39.5 kg of (R)-methyl 2-(2-(benzyloxycarbonylamino)ethylamino)-3-t-butoxypropanoate was dissolved in 276 L of methanol in a reactor; purged with nitrogen; 5.9 kg of palladium/carbon (10% water mixture) was added and stirred for 3 hours while the hydrogen pressure was maintained at 10 bar. The reaction solution was filtered, concentrated under reduced pressure, and then again azeotroped by adding 30 L of isopropylether. 158 L (115 kg) of isopropylether, 39 L (35 kg) of ethyl acetate, and 36.4 kg of silica gel were added to a concentrated solution, stirred for 1 hour, decompression-filtered, and then concentrated under reduced pressure. A concentrated residue was azeotroped by adding 30 L of methanol, and then a concentrated solution and 221 L of methanol were added to a reactor. After purging with nitrogen, 11.85 kg of palladium/carbon (10% water mixture) was added, and then stirred for 6 hours while hydrogen pressure was maintained at 15 bar. The reaction solution was filtered, and then concentrated under reduced pressure. An aqueous layer was isolated in twice by adding 80 L of isopropylether and 80 L of purified water to the concentrated solution. An organic layer was isolated after adding methylene chloride/isopropanol=5:1 (126 L) to the aqueous layer and then stirring in 5 times. The organic layer was dehydration-filtered with 50 kg of sodium sulfate to obtain 9.7 kg of a title compound.

$^1$H NMR (400 MHz, CDCl$_3$) δ 6.41 (brs, 1H), 3.76 (m, 3H), 3.63 (m, 1H), 3.52 (m, 1H), 3.42 (m, 1H), 3.28 (m, 1H), 3.16 (m, 1H), 2.95 (m, 1H), 2.45 (brs, 1H), 1.17 (s, 9H)

Step 5: Preparation of (R)-3-(t-butoxymethyl)piperazine-2-one di-p-toluoyl-L-tartrate (Chemical Formula 3)

A solution that was prepared by dissolving 100.0 g of (R)-3-(t-butoxymethyl)piperazine-2-one to 500 mL of acetone, and then by dissolving 207.4 g of di-p-toluoyl-L-tartaric acid to 700 mL of acetone was slowly added to a reactor. The resulting reaction solution was stirred for 1 hour, and then resulting solid was filtered to obtain 251.4 g of a title compound.

$^1$H NMR (400 MHz, DMSO) δ 8.03 (brs, 1H), 7.83 (d, 4H), 7.32 (d, 4H), 5.67 (s, 2H), 3.55-3.66 (m, 3H), 3.18-3.29 (m, 3H), 3.04 (m, 1H), 2.36 (s, 6H), 1.10 (s, 9H)<

Example 6

Preparation of (R)-4-[(R)-3-amino-4-(2,4,5-trifluorophenyl)butanoyl]-3-(t-butoxymethyl)piperazine-2-one (Chemical Formula 1) Hydrochloride Step 1: Preparation of t-butyl(R)-4-[(R)-2-(t-butoxymethyl)-3-oxopiperazine-1-yl]-4-oxo-1-(2,4,5-trifluorophenyl)butane-2-ylcarbamate 1.0 g of (R)-3-t-butoxycarbonylamino-4-(2,4,5-trifluorophenyl)butanoic acid (Chemical Formula 2) was dissolved in 15 mL of methylene chloride, and then the resulting reaction solution was cooled to 0° C. While the reaction solution was stirred, 0.43 mL of 4-methylmorpholine was dropped; after 10 minutes, 0.47 mL of isobutylchloroformate was dropped; and then stirred for 1 hour. The resulting solid was filtered with diatomite; was washed with 5 mL of methylene chloride; and then the filtrate was cooled to 0° C. A solution that was prepared by dissolving 838 mg of (R)-(3-t-butoxymethyl)piperazine-2-one (Chemical Formula 3) to 3 mL of tetrahydrofuran and 1.1 mL of diisopropylethylamine were added to the cooled filtrate, and then stirred for 1 hour. Next, it was diluted with 20 ml of ethyl acetate; washed with brine in twice; and then an organic layer was dehydration-concentrated with magnesium sulfate. A residue was purified with column chromatography to obtain 838 mg of a title compound.

$^1$H NMR (400 MHz, CDCl$_3$) δ 7.03 (m, 1H), 6.88 (m, 1H), 5.97 (m, 1H), 5.48 (m, 1H), 4.16-4.07 (m, 1H), 4.02-3.91 (m, 1H), 3.74 (m, 2H) 3.37 (m, 2H), 3.24 (m, 1H), 2.92 (m, 2H), 2.80 (m, 1H), 2.59 (m, 2H), 1.34 (d, 9H), 1.13 (s, 9H)

Step 2: Preparation of (R)-4-[(R)-3-amino-4-(2,4,5-trifluorophenyl)butanoyl]-3-(t-butoxymethyl)piperazine-2-one (Chemical Formula 1) Hydrochloride 97 mg of t-butyl(R)-4-[(R)-2-(t-butoxymethyl)-3-oxopiperazine-1-yl]-4-oxo-1-(2,4,5-trifluorophenyl)butane-2-ylcarbamate of the above Step 1 was dissolved in 3 mL of methanol, 2 mL of 2N-hydrochloric acid/diethyl ether was added, and then stirred for 3 hours at room temperature. The resulting reaction mixture was concentrated and decompression-dried to obtain 64 mg of a title compound as a foaming solid.

$^1$H NMR (400 MHz, CD$_3$OD) δ 7.37 (m, 1H), 7.23 (m, 1H), 4.80 (m, 1H), 4.59-4.40 (m, 1H), 3.93 (m, 1H), 3.90-3.83 (m, 2H), 3.70 (m, 1H), 3.38 (m, 2H), 3.27 (m, 1H), 3.07 (m, 2H), 2.89-2.66 (m, 2H), 1.18 (s, 3H), 1.11 (s, 6H)

Mass (M+1): 402

Example 7

Preparation of (R)-4-[(R)-3-amino-4-(2,4,5-trifluorophenyl)butanoyl]-3-(t-butoxymethyl)piperazine-2-one (Chemical Formula 1)

Step 1: Preparation of benzyl(R)-4-[(R)-2-(t-butoxymethyl)-3-oxopiperazine-1-yl]-4-oxo-1-(2,4,5-trifluorophenyl)butane-2-ylcarbamate 65.7 g of a title compound was obtained by using the same method with that of Step 1 of Example 6, except that 50.0 g of (R)-3-(benzyloxycarbonylamino)-4-(2,4,5-trifluorophenyl) butanoic acid and 85.7 g of (R)-(3-t-butoxymethyl)piperazine-2-one di-p-toluoyl-L-tartarate were used instead of (R)-3-t-butoxycarbonylamino-4-(2,4,5-trifluorophenyl)butanoic acid and (R)-(3-t-butoxylmethyl)piperazine-2-one, respectively, in Step 1 of Example 6.

$^1$H NMR (400 MHz, CDCl$_3$) δ 7.20~7.38 (m, 5H), 7.04 (m, 1H), 6.86 (m, 1H), 6.74 and 6.61 (br s, 1H), 5.79 (m, 1H), 5.00 (m, 2H), 4.91 and 4.69 (m, 1H), 4.41 and 4.25 (m, 1H), 4.16 and 3.99 (m, 1H), 3.68-3.90 (m, 3H), 3.21-3.38 (m, 2H), 2.96-3.12 (m, 2H), 2.59-2.90 (m, 2H), 1.45 and 1.11 (s, 9H)

Step 2: Preparation of (R)-4-[(R)-3-amino-4-(2,4,5-trifluorophenyl) butanoyl]-3-(t-butoxymethyl)piperazine-2-one (Chemical Formula 1)

65.7 g of benzyl(R)-4-[(R)-2-(t-butoxymethyl)-3-oxopiperazine-1-yl]-4-oxo-1-(2,4,5-trifluorophenyl)butane-2-ylcarbamate of the above Step 1 was dissolved in 409 mL of methanol; a solution in which 13.1 g of palladium/carbon was wetted with 92 ml of ethyl acetate was added; and then stirred for 2 hours under hydrogen pressure of 15 bar. The resulting reaction solution was filtered with diatomite, and then concentrated under reduced pressure to obtain 34.8 g of a title compound.

$^1$H NMR (400 MHz, CD$_3$OD) δ 7.27 (m, 1H), 7.14 (m, 1H), 4.56-4.39 (m, 1H), 3.96-3.81 (m, 3H), 3.70 (m, 1H), 3.46 (m, 1H), 3.43-3.32 (m, 1H), 2.83-2.65 (m, 3H), 2.58-2.40 (m, 2H), 1.16 (s, 3H), 1.11 (s, 6H)

Mass (M+1): 402

Example 8

Preparation of (R)-4-[(R)-3-amino-4-(2,4,5-trifluoromethyl)butanoyl]-3-(t-butoxymethyl)piperazine-2-one (Chemical Formula 1) Tartrate

Step 1: Prepartion of (R)-4-[(R)-3-amino-4-(2,4,5-trifluorophenyl) butanoyl]-3-(t-butoxymethyl)piperazine-2-one (Chemical Formula 1)

60 mg of hydrochloride compound represented by Chemical Formula 1 obtained from Example 6 was added to 10 mL of 5% sodium hydrogen carbonate aqueous solution; 10 mL of dichloromethane/2-propanol [4/1(v/v)] mixed solution was added; was extracted in twice to obtain an organic layer; and then the organic layer was decompression-dried to obtain 55 mg of a title compound as a solid.

$^1$H NMR (400 MHz, CD$_3$OD) δ 7.27 (m, 1H), 7.14 (m, 1H), 4.56-4.39 (m, 1H), 3.96-3.81 (m, 3H), 3.70 (m, 1H), 3.46 (m, 1H), 3.43-3.32 (m, 1H), 2.83-2.65 (m, 3H), 2.58-2.40 (m, 2H), 1.16 (s, 3H), 1.11 (s, 6H)

Mass (M+1): 402

Step 2: Preparation of (R)-4-[(R)-3-amino-4-(2,4,5-trifluorophenyl) butanoyl]-3-(t-butoxymethyl)piperazine-2-one (Chemical Formula 1) Tartrate 55 mg of the compound of the above Step 1 or Example 7 was dissolved in 0.56 mL of acetone; the solution that was prepared by dissolving 26 mg of L-tartaric acid to 0.35 mL of ethanol/water [9/1(v/v)] was slowly added; and then stirred for 30 minutes. 0.56 mL of 2-propanol was again added thereto; stirred for 10 minutes; and then filtered to obtain 77 mg of a title compound as a solid.

$^1$H NMR (400 MHz, CD$_3$OD) δ 7.38 (m, 1H), 7.22 (m, 1H), 4.80 (m, 1H), 4.59-4.40 (m, 1H), 4.40 (s, 2H), 3.93 (m, 1H), 3.90-3.83 (m, 2H), 3.70 (m, 1H), 3.38 (m, 2H), 3.27 (m, 1H), 3.07 (m, 2H), 2.89-2.66 (m, 2H), 1.15 (s, 3H), 1.11 (s, 6H)

Mass (M+1): 402

What is claimed is:

1. A method for manufacturing dipeptidyl peptidase-IV inhibitor represented by Chemical Formula 1 comprising:
   (Step 1) reacting a compound represented by Chemical Formula 2 and a compound represented by Chemical Formula 3 in the presence of isochloroformate, a base and a reaction solvent to prepare a compound represented by Chemical Formula 4; and
   (Step 2) removing an amine-protecting group of the compound represented by Chemical Formula 4 produced in the above Step 1 to prepare a compound represented by Chemical Formula 1,

[Chemical Formula 1]

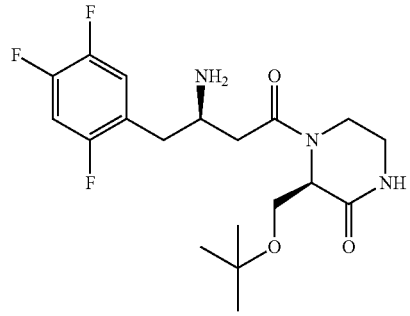

[Chemical Formula 2]

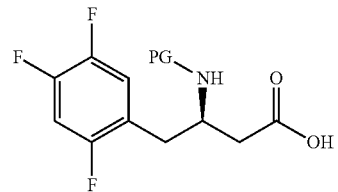

-continued

[Chemical Formula 3]

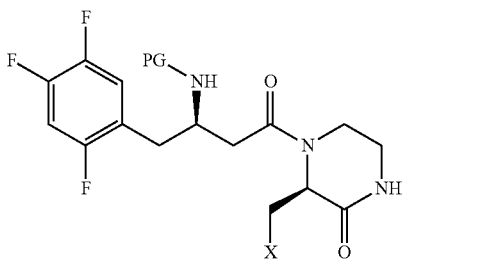

[Chemical Formula 4]

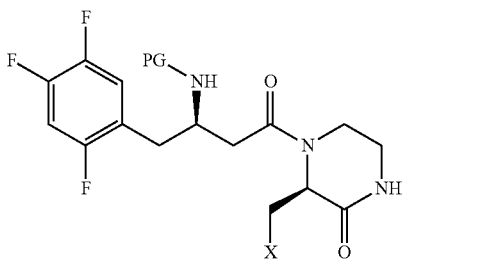

[Chemical Formula 2]

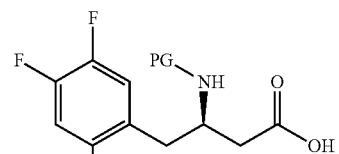

[Chemical Formula 5]

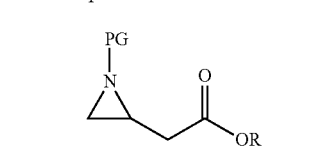

[Chemical Formula 6]

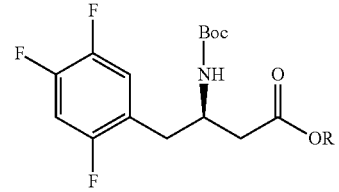

wherein
PG is a protecting group;
X is $OR^1$, $SR^1$ or $NR^1R^2$,
wherein $R^1$ and $R^2$ are each independently $C_1$-$C_5$ lower alkyl, or, in the case of $NR^1R^2$, $R^1$ and $R^2$ may be 5-membered ring to 7-membered ring containing O; and
HY is a free acid.

2. The method as set forth in claim 1, wherein the reaction solvent in (Step 1) is selected from the group consisting of toluene, tetrahydrofuran, methylene chloride, acetonitrile, and N,N-dimethylformamide.

3. The method as set forth in claim 1, wherein the base in (Step 1) is selected from the group consisting of N-methyl morpholine, isopropylethylamine, triethylamine, pyridine and a combination thereof.

4. The method as set forth in claim 1, wherein the reaction of Step 1 is performed at −20° C. to room temperature.

5. The method as set forth in claim 1, wherein the amine-protecting group is butoxycarbonyl (Boc) or benzyloxycarbonyl (Cbz).

6. The method as set forth in claim 1, wherein the amine-protecting group is butoxycarbonyl (Boc) and the amine-protecting group is removed by reacting the compound represented by Chemical Formula 4 with trifluoroacetic acid/dichloromethane, ethyl acetate/hydrogen chloride, diethylether/hydrogen chloride, hydrogen chloride/dichloromethane or methanol/hydrogen chloride.

7. The method as set forth in claim 1, wherein the amine-protecting group is benzyloxycarbonyl (Cbz) and the amine-protecting group is removed by reacting the compound represented by Chemical Formula 4 with hydrogen in the presence of palladium/carbon.

8. The method as set in claim 1, the compound represented by Chemical Formula 2 is prepared by a method comprising:
(Step a) opening aziridine ring using Grignard reagent in a compound represented by Chemical Formula 5 to prepare a compound represented by Chemical Formula 6; and
(Step b) hydrolyzing the compound represented by Chemical Formula 6 prepared in (Step a) and introducing an amine-protecting group to prepare a compound represented by Chemical Formula 2, wherein
PG is a protecting group; and
R is a lower alkyl of $C_1$-$C_5$.

9. The method as set forth in claim 8, wherein the amine-protecting group is butoxycarbonyl (Boc) or benzyloxycarbonyl (Cbz).

10. The method as set forth in claim 1, the compound represented by Chemical Formula 3 is prepared by a method comprising:
(Step a') reacting a compound represented by Chemical Formula 7 with an amine group-protected aminoaldehyde compound and an reduction reagent to prepare a compound represented by Chemical Formula 8; and
(Step b') removing the amine-protecting group by triggering a hydrogen reaction in the compound represented by Chemical Formula 8, and inducing a cyclization to prepare a compound represented by Chemical Formula 3 or salt thereof,

[Chemical Formula 3]

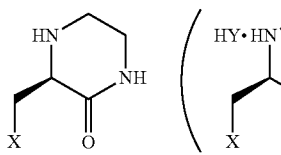

[Chemical Formula 7]

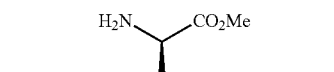

[Chemical Formula 8]

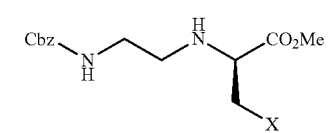

wherein
X is $OR^1$, $SR^1$ or $NR^1R^2$, wherein $R^1$ and $R^2$ are each independently a lower alkyl of $C_1$-$C_5$, in the case of $NR^1R^2$, $R^1$ and $R^2$ may be 5-membered ring to 7-membered ring containing hetero atom, O; and HY is a free acid.

11. The method as set forth in claim 10, wherein the hydrogen reaction uses palladium/carbon.

12. An intermediate represented by the following Chemical Formula 8 produced in the process of preparing the compound represented by Chemical Formula 3 as set forth in claim 10:

[Chemical Formula 8]

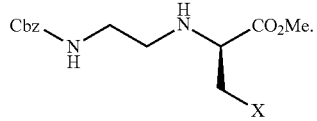

* * * * *